US00PP28525P3

(12) United States Plant Patent
Holtmaat

(10) Patent No.: US PP28,525 P3
(45) Date of Patent: Oct. 10, 2017

(54) ***ECHINACEA* PLANT NAMED 'ECHCHER298'**

(50) Latin Name: *Echinacea purpurea*
Varietal Denomination: Echcher298

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 71 days.

(21) Appl. No.: 14/756,666

(22) Filed: Sep. 29, 2015

(65) Prior Publication Data

US 2017/0094884 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

New Plants and Flowers Cherry-coloured hue and a lime-green centre Aug. 17, 2015, retrieved on Jan. 19, 2017, retrieved from the Internet at <http://www.newplantsandflowers.com/cherry-coloured-hue-and-a-lime-green-centre/> 2 pp.*
Upov Pluto Plant Variety Database Jan. 17, 2017 retrieved on Jan. 19, 2017, retrieved from the Internet at <www.3.wipo.int/pluto/user/en/index.jsp> one page.*

* cited by examiner

*Primary Examiner* — June Hwu
(74) *Attorney, Agent, or Firm* — C. A. Whealy

(57) ABSTRACT

A new and distinct cultivar of *Echinacea* plant named 'Echcher298', characterized by its upright plant habit; moderately vigorous growth habit; freely branching habit; strong flowering stems; numerous large anemone-centered inflorescences with pale yellow green to white and light pink-colored florets; and good garden performance.

2 Drawing Sheets

Botanical designation: *Echinacea purpurea.*
Cultivar denomination: 'ECHCHER298'.

BACKGROUND OF THE INVENTION

The present invention relates to a new and distinct cultivar of *Echinacea* plant, botanically known as *Echinacea purpurea*, and hereinafter referred to by the name 'Echcher298'.

The new *Echinacea* plant is a product of a planned breeding program conducted by the Inventor in Zuidwolde, The Netherlands. The objective of the breeding program is to develop new freely flowering *Echinacea* plants with unique and attractive ray floret coloration.

The new *Echinacea* plant originated from an open-pollination in June, 2012 in Zuidwolde, The Netherlands of *Echinacea purpurea* 'Meringue', disclosed in U.S. Plant Pat. No. 20,537, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in Zuidwolde, The Netherlands in July, 2013.

Asexual reproduction of the new *Echinacea* plant by in vitro meristem culture in a controlled environment in Zuidwolde, The Netherlands since December, 2013 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Echcher298'. These characteristics in combination distinguish 'Echcher298' as a new and distinct *Echinacea* plant:

1. Upright plant habit.
2. Moderately vigorous growth habit.
3. Freely branching habit.
4. Strong flowering stems.
5. Numerous large anemone-centered inflorescences with pale yellow green to white and light pink-colored florets.
6. Good garden performance.

Plants of the new *Echinacea* can be compared to plants of the female parent, 'Meringue'. Plants of the new *Echinacea* differ from plants of 'Meringue' in the following characteristics:

1. Plants of the new *Echinacea* are taller than plants of 'Meringue'.
2. Plants of the new *Echinacea* flower later than plants of 'Meringue'.
3. Plants of the new *Echinacea* and 'Meringue' differ in floret color as plants of 'Meringue' have yellow green-colored florets.

Plants of the new *Echinacea* can be compared to plants of *Echinacea purpurea* 'Coconut Lime', disclosed in U.S. Plant Pat. No. 18,617. In side-by-side comparisons conducted in Zuidwolde, The Netherlands, plants of the new *Echinacea* differed primarily from plants of 'Coconut Lime' in the following characteristics:

1. Plants of the new *Echinacea* were not as freely branching as plants of 'Coconut Lime'.
2. Plants of the new *Echinacea* had larger inflorescences than plants of 'Coconut Lime'.
3. Plants of the new *Echinacea* and 'Coconut Lime' differed in floret color as plants of 'Coconut Lime' had white and yellow green-colored florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Echcher298' grown in ground beds in an outdoor nursery and placed in a 21 cm container for the photograph.

The photographs on the second sheet are close-up views of a typical inflorescence (upper photograph) and the upper surface of a typical leaf (lower photograph) of 'Echcher298'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 30° C. and night temperatures ranged from 8° C. to 18° C. Plants were eight months old when the photographs and description were taken. In the following description, color references are made to The Royal Horticultural Society Colour Chart, 2007 Edition, except where general terms of ordinary dictionary significance are used.

Botanical classification: *Echinacea purpurea* 'Echcher298'.

Parentage:

*Female parent*.—*Echinacea purpurea* 'Meringue', disclosed in U.S. Plant Pat. No. 20,537.

*Male parent*.—Unknown selection of *Echinacea purpurea*, not patented.

Propagation:

*Type*.—By in vitro meristem culture.

*Time to initiate roots, summer*.—About one week at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Herbaceous perennial; upright plant habit, narrow inverted triangle; freely branching habit with about five primary branches developing per plant; moderately vigorous growth habit.

*Plant height*.—About 67.3 cm.

*Plant diameter or spread*.—About 48.3 cm.

*Lateral branches*.—Length: About 46.2 cm. Diameter: About 4 mm. Internode length: About 6.4 cm. Aspect: Erect to about 10° from vertical. Strength: Strong. Texture: Sparsely to moderately pubescent, strigose; slightly rough. Color: Close to 144A to 144B; stripes, close to 143B.

Leaf description:

*Basal leaves*.—Arrangement: Alternate, simple. Length: About 16.7 cm. Width: About 4.6 cm. Shape: Elliptic. Apex: Acute. Base: Attenuate. Margin: Entire; slightly to moderately undulate. Texture and luster, upper surface: Moderately pubescent, rough; slightly glossy. Texture and luster, lower surface: Moderately pubescent, rough; moderately glossy. Venation pattern: Pinnate. Color: Developing leaves, upper surface: Close to 143A. Developing leaves, lower surface: Close to 143B. Fully expanded leaves, upper surface: Close to NN137D; venation, close to 144A. Fully expanded leaves, lower surface: Close to 147B; venation, close to 145B.

*Petioles, basal leaves*.—Length: About 9.3 cm. Diameter: About 3 mm. Height: About 3 mm. Strength: Strong, flexible. Texture and luster, upper surface: Mostly glabrous except for margins which are sparsely pubescent; slightly glossy. Texture and luster, lower surface: Glabrous; matte. Color, upper surface: Close to 144B, towards the margins, close to 143A. Color, lower surface: Close to 144A.

*Cauline leaves*.—Arrangement: Alternate, simple. Length: About 11.7 cm. Width: About 2 cm. Shape: Elliptic. Apex: Acute. Base: Attenuate. Margin: Entire; slightly to moderately undulate. Texture and luster, upper surface: Moderately pubescent, rough; slightly glossy. Texture and luster, lower surface: Moderately pubescent, rough; moderately glossy. Venation pattern: Pinnate. Color: Developing leaves, upper surface: Close to 143A. Developing leaves, lower surface: Close to 143B. Fully expanded leaves, upper surface: Close to NN137D; venation, close to 144A. Fully expanded leaves, lower surface: Close to 147B; venation, close to 145B.

*Petioles, cauline leaves*.—Length: About 1.6 cm. Diameter: About 2 mm. Height: About 2 mm. Strength: Strong, flexible. Texture and luster, upper surface: Mostly glabrous except for margins which are sparsely pubescent; slightly glossy. Texture and luster, lower surface: Glabrous; matte. Color, upper surface: Close to 144B, towards the margins, close to 143A. Color, lower surface: Close to 144A.

Inflorescence description:

*Appearance*.—Large anemone-centered inflorescences with ray and disc florets arranged on a capitulum; inflorescences positioned upright above the foliar plane on mostly upright and strong peduncles.

*Flowering habit*.—Freely flowering habit with about 30 inflorescences developing per plant during the flowering season.

*Fragrance*.—None detected.

*Time to flower*.—In the garden, plants flower continuously from early July to late September in The Netherlands.

*Inflorescence longevity*.—Inflorescences maintain good substance for about three weeks on the plant; inflorescences persistent.

*Inflorescence buds*.—Height: About 1.9 cm. Diameter: About 2.4 cm. Shape: Flattened globular. Color: Involucral bracts, close to between 144A and 146A; ray florets, close to 150B.

*Inflorescence size*.—Diameter: About 11.5 cm. Depth (height): About 6.1 cm. Disc diameter: About 7 cm. Receptacle height: About 1 cm. Receptacle diameter: About 1 cm. Receptacle color: Close to NN155A.

*Ray florets*.—Quantity and arrangement: About 18 arranged in a single whorl at the base of the receptacle. Length: About 5.3 cm. Width: About 8mm. Shape: Oblanceolate. Apex: Cleft to deeply praemorse. Base: Cuneate. Margin: Entire. Texture, upper surface: Smooth, glabrous; slightly velvety. Texture, lower surface: Glabrous; longitudinally ridged. Luster, upper surface: Matte. Luster, lower surface: Slightly glossy. Aspect: Horizontal to drooping, about 30° from horizontal. Color: When opening, upper surface: Close to between 150D and 155A. When opening, lower surface: Close to 150C. Fully opened, upper surface: Close to 62C to 62D; color does not change with development. Fully opened, lower surface: Close to 150C flushed with close to 62C; color does not change with development.

*Disc florets*.—Quantity and arrangement: About 300 per inflorescence, spirally at the center. Length: About 2.7 cm. Diameter: About 4 mm. Shape: Oblanceolate. Apex: Narrowly acute to praemorse. Base: Cuneate. Margin: Entire. Texture, upper surface: Smooth, glabrous; slightly velvety. Texture, lower surface: Smooth, glabrous. Luster, upper surface: Matte. Luster, lower surface: Slightly glossy. Color: When opening, upper surface: Close to between 150D and 155A. When opening, lower surface: Close to 150C. Fully opened, upper surface: Close to 62C; color does not change with development. Fully opened, lower surface: Close to 150C flushed with close to 62C; color does not change with development.

*Receptacle spines*.—Quantity: One per disc floret. Shape: Acicular. Apex: Acute. Base: Attenuate. Texture: Smooth, glabrous. Luster: Glossy. Color: Close to 143B; towards the apex, close to 13A and at the apex, close to 33A.

*Involucral bracts*.—Quantity per inflorescence: About 72 arranged in about three whorls. Length: About 1.1 cm. Width: About 3 mm. Shape: Ovate to narrowly ovate. Apex: Acute. Base: Cuneate. Margin: Entire. Texture, upper surface: Smooth, glabrous. Texture, lower surface: Moderately pubescent. Color, upper surface: Close to 137B. Color, lower surface: Close to 137A.

*Peduncles*.—Length: About 13.4 cm. Diameter: About 5 mm. Strength: Strong. Aspect: Upright to about 15° from vertical. Texture: Sparsely to moderately pubescent, strigose. Color: Close to 144A to 144B; stripes, close to 143B.

*Reproductive organs*.—Androecium: None observed on ray or disc florets. Gynoecium (present only on disc florets): Quantity per floret: One. Pistil length: About 7 mm. Stigma shape: Decurrent, unequal. Stigma color: Close to N186C and darker than N186C. Style length: About 5.5 mm. Style color: Close to 145B. Ovary color: Close to 144A. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Echcher298' as illustrated and described.

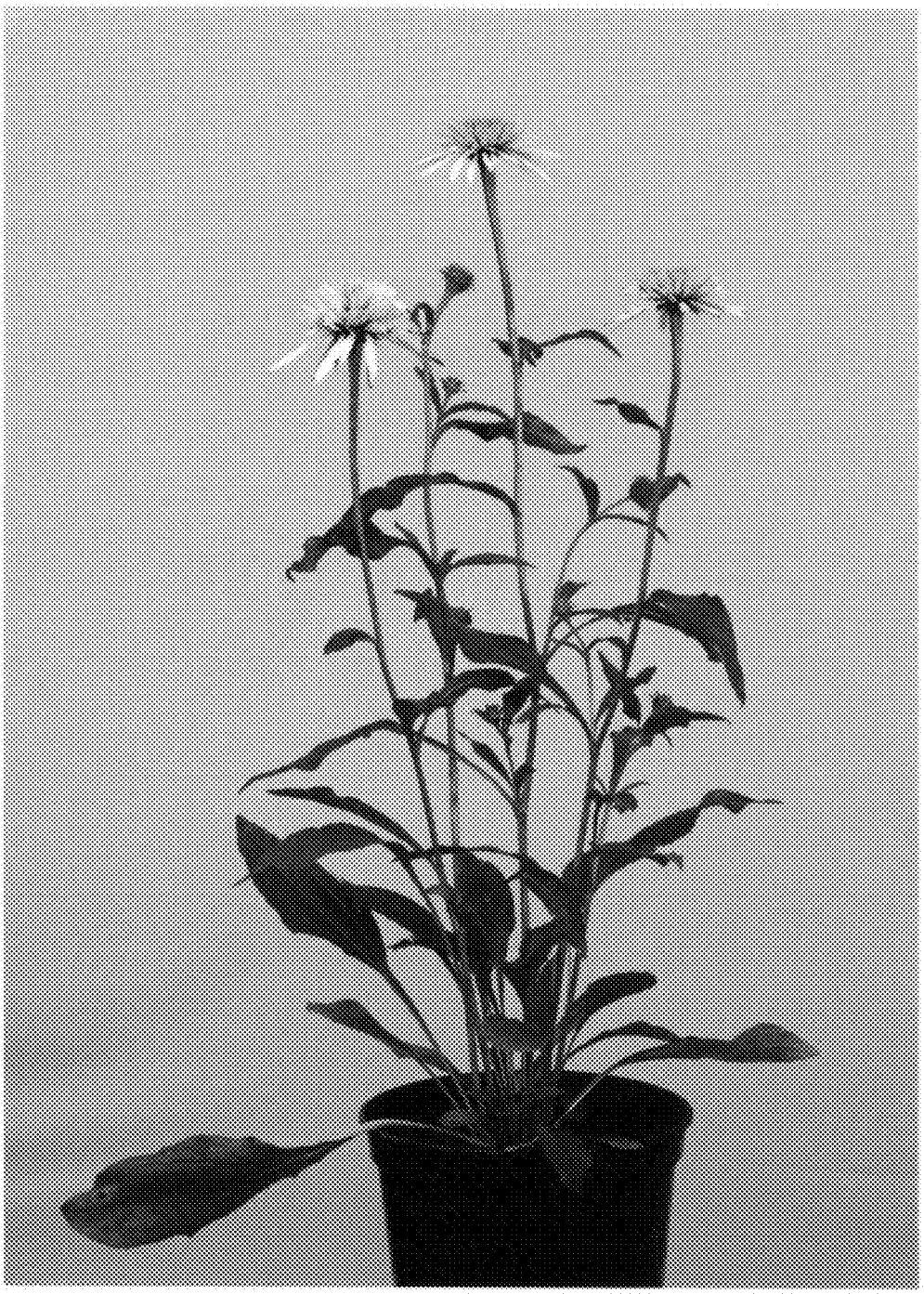

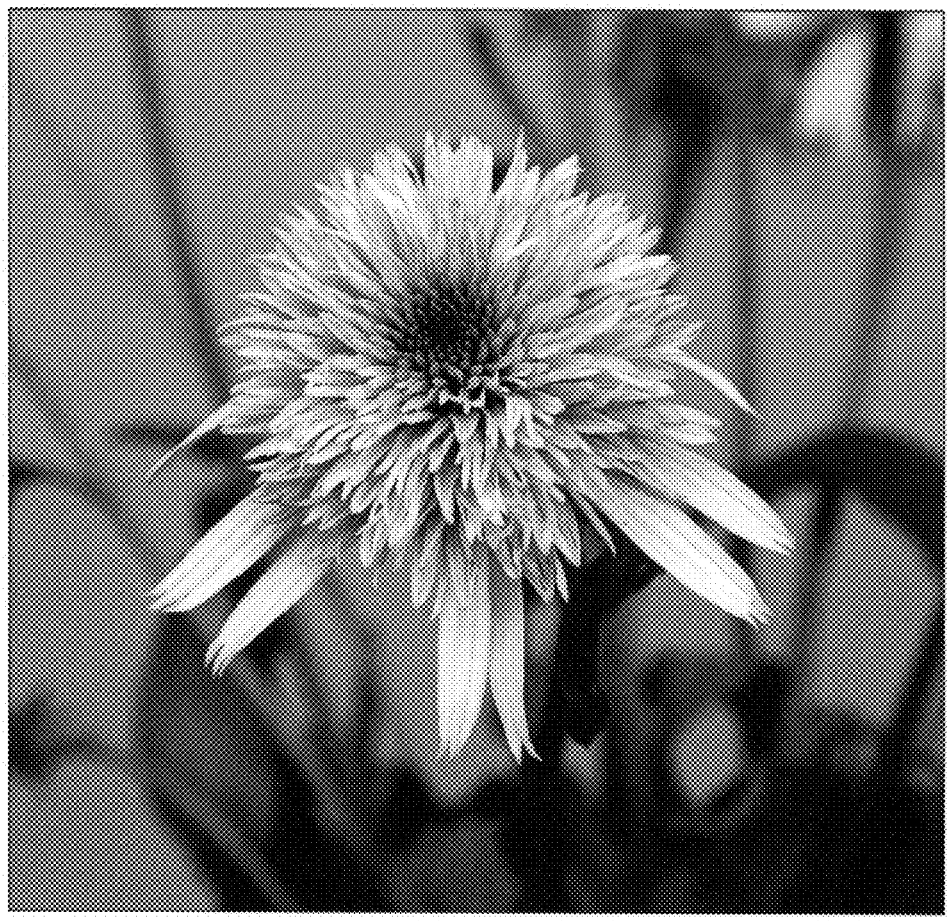
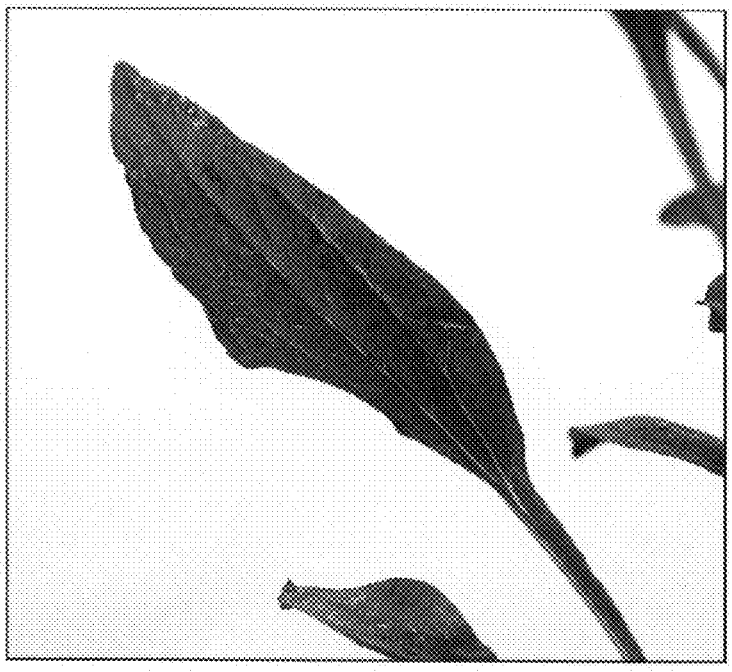

* * * * *